US010578692B2

United States Patent
Tsujita et al.

(10) Patent No.: US 10,578,692 B2
(45) Date of Patent: Mar. 3, 2020

(54) MRI GRADIENT COIL HAVING NON-UNIFORM COOLANT PASSAGEWAY WITHIN GRADIENT COIL CONDUCTOR

(71) Applicant: TOSHIBA MEDICAL SYSTEMS CORPORATION, Otawara-shi, Tochigi (JP)

(72) Inventors: Kazuhiko Tsujita, Tochigi (JP); Yoshitomo Sakakura, Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 829 days.

(21) Appl. No.: 14/631,264

(22) Filed: Feb. 25, 2015

(65) Prior Publication Data

US 2015/0177347 A1    Jun. 25, 2015

Related U.S. Application Data

(63) Continuation of application No. PCT/JP2013/072126, filed on Aug. 19, 2013.

(30) Foreign Application Priority Data

Aug. 27, 2012   (JP) .................... 2012-186967

(51) Int. Cl.
*G01R 33/385*    (2006.01)
*A61B 5/055*    (2006.01)
*G01R 33/48*    (2006.01)

(52) U.S. Cl.
CPC ......... *G01R 33/3856* (2013.01); *A61B 5/055* (2013.01); *G01R 33/3858* (2013.01); *G01R 33/4822* (2013.01); *Y10T 156/10* (2015.01)

(58) Field of Classification Search
USPC ................. 324/300–322; 600/407–435; 382/128–131
See application file for complete search history.

(56) References Cited

U.S. PATENT DOCUMENTS 5,304,933 A * 4/1994 Vavrek ............... G01R 33/385
                                                        324/300
5,489,848 A    2/1996 Furukawa ................. 324/318
(Continued)

FOREIGN PATENT DOCUMENTS

CN    1875288 A    12/2006
CN    101295011 A    10/2008
(Continued)

OTHER PUBLICATIONS

Office Action dated Mar. 31, 2016 in CN Patent Application No. 201380002710.1.
(Continued)

*Primary Examiner* — Melissa J Koval
*Assistant Examiner* — Tiffany A Fetzner
(74) *Attorney, Agent, or Firm* — Nixon & Vanderhye P.C.

(57) ABSTRACT

According to one embodiment, a gradient coil unit for a magnetic resonance imaging apparatus includes gradient coils for forming gradient magnetic fields in mutually orthogonal three axis directions. At least one of the gradient coils includes a conductor part along a coil pattern and a holding part holding the coil pattern. A passage of a coolant is formed inside at least one of the conductor part and the holding part. The passage has a non-constant cross section.

13 Claims, 5 Drawing Sheets

(56) References Cited

U.S. PATENT DOCUMENTS

| | | | | |
|---|---|---|---|---|
| 6,236,207 B1* | 5/2001 | Arz | .................... | G01R 33/3856 324/318 |
| 6,311,389 B1* | 11/2001 | Uosaki | ............... | G01R 33/3858 29/605 |
| 6,741,152 B1 | 5/2004 | Arz et al. | ...................... | 335/300 |
| 6,744,631 B1* | 6/2004 | Chuang | ................... | G06F 1/203 165/80.3 |
| 6,771,072 B2 | 8/2004 | Schuster | ............ | G01R 33/3856 324/318 |
| 7,180,292 B2 | 2/2007 | Coughlin | ..................... | 324/318 |
| 7,370,789 B2 | 5/2008 | Ham | ............................ | 324/318 |
| 7,489,131 B2 | 2/2009 | Lvovsky | ....................... | 324/307 |
| 8,736,266 B2 | 5/2014 | Sakakura | ..................... | 324/318 |
| 9,075,119 B2* | 7/2015 | Terada | ................. | G01R 33/385 |
| 10,222,436 B2* | 3/2019 | Yang | .................. | G01R 33/3858 |
| 2001/0033168 A1* | 10/2001 | Heid | .................. | G01R 33/3856 324/322 |
| 2003/0141870 A1* | 7/2003 | Schuster | ............ | G01R 33/3856 324/318 |
| 2003/0206018 A1* | 11/2003 | Gebhardt | ........... | G01R 33/3873 324/318 |
| 2007/0236218 A1 | 10/2007 | Liu | ................................ | 324/318 |
| 2007/0268021 A1* | 11/2007 | Sakakura | ............. | G01R 33/288 324/322 |
| 2010/0321019 A1 | 12/2010 | Imamura et al. | ............. | 324/318 |
| 2011/0121832 A1 | 5/2011 | Shvartsman et al. | ......... | 324/318 |
| 2012/0176137 A1* | 7/2012 | Terada | ................. | G01R 33/385 324/322 |
| 2014/0061202 A1* | 3/2014 | Mathieu | ............. | G01R 33/3804 220/560.09 |
| 2015/0177347 A1* | 6/2015 | Tsujita | ............... | G01R 33/3856 324/322 |

FOREIGN PATENT DOCUMENTS

| | | |
|---|---|---|
| JP | 2009-112870 | 5/2009 |
| JP | 2010-263955 | 11/2010 |
| WO | 2008/096628 A1 | 8/2008 |

OTHER PUBLICATIONS

Office Action dated Jul. 31, 2015 in CN Patent Application No. 201380002710.1.

First Japanese office action dated Jul. 4, 2017, in Patent Application No. JP 2013-170006.

Non-English International Search Report including Written Opinion of the ISA for PCT/JP2013/072126, dated Nov. 19, 2013, six pages.

Notification of Transmittal of Translation of the International Preliminary Report on Patentability in PCT/JP2013/072126 dated Mar. 12, 2015.

Japanese final rejection dated Jan. 23, 2018, in Patent Application No. JP 2013-170006.

* cited by examiner

MRI GRADIENT COIL HAVING NON-UNIFORM COOLANT PASSAGEWAY WITHIN GRADIENT COIL CONDUCTOR

CROSS REFERENCES TO RELATED APPLICATIONS

This is a continuation of Application PCT/JP2013/72126, filed on Aug. 19, 2013.

This application is based upon and claims the benefit of priority from Japanese Patent Application No. 2012-186967, filed on Aug. 27, 2012; the entire contents of which are incorporated herein by reference.

FIELD

Embodiments described herein relate generally to an MRI (magnetic resonance imaging) apparatus, a gradient coil unit for a magnetic resonance imaging apparatus and a method for manufacturing a gradient coil unit for a magnetic resonance imaging apparatus.

BACKGROUND

The MRI apparatus is an imaging diagnostic apparatus which magnetically excites nuclear spins of an object set in a static magnetic field with RF (radio frequency) signals having the Larmor frequency and reconstructs an image based on MR (magnetic resonance) signals generated due to the excitation.

In the MRI apparatus, the gradient coil to apply gradient magnetic fields to an imaging area produces heat during an operation. Accordingly, a pipe of cooling water is provided spirally next to the main coil, which composes the gradient coil, and the gradient coil is cooled by the circulation of the cooling water.

PRIOR TECHNICAL LITERATURE

[Patent literature 1] JPA 2010-263955
[Patent literature 2] JPA 2011-087915

It is an object of the present invention to provide a magnetic resonance imaging apparatus which can cool a gradient coil more effectively, a gradient coil unit, for a magnetic resonance imaging apparatus, which can be cooled more effectively, and a method for manufacturing a gradient coil unit, for a magnetic resonance imaging apparatus, which can be cooled more effectively.

DETAILED DESCRIPTION

In general, according to one embodiment, a gradient coil unit for a magnetic resonance imaging apparatus includes gradient coils for forming gradient magnetic fields in mutually orthogonal three axis directions. At least one of the gradient coils includes a conductor part along a coil pattern and a holding part holding the coil pattern. A passage of a coolant is formed inside at least one of the conductor part and the holding part. The passage has a non-constant cross section.

Further, according to another embodiment, a gradient coil unit for a magnetic resonance imaging apparatus includes gradient coils for forming gradient magnetic fields in mutually orthogonal three axis directions. At least one of the gradient coils includes a conductor part along a coil pattern and a holding part holding the coil pattern. A passage of a coolant is formed. At least a part of the conductor part forms a wall surface of the passage.

Further, according to another embodiment, a magnetic resonance imaging apparatus includes the gradient coil unit and an imaging system. The imaging system is configured to perform magnetic resonance imaging of an object using the gradient coil unit.

Further, according to another embodiment, a method for manufacturing a gradient coil unit for a magnetic resonance imaging apparatus includes: laminating platy members forming a void corresponding to a passage of a coolant; and bonding the laminated platy members. Each of the platy members consists of a conductive material.

A magnetic resonance imaging apparatus, a gradient coil unit for a magnetic resonance imaging apparatus and a method for generating a gradient coil unit for a magnetic resonance imaging apparatus according to embodiments of the present invention will be described with reference to the accompanying drawings.

Figure 1:
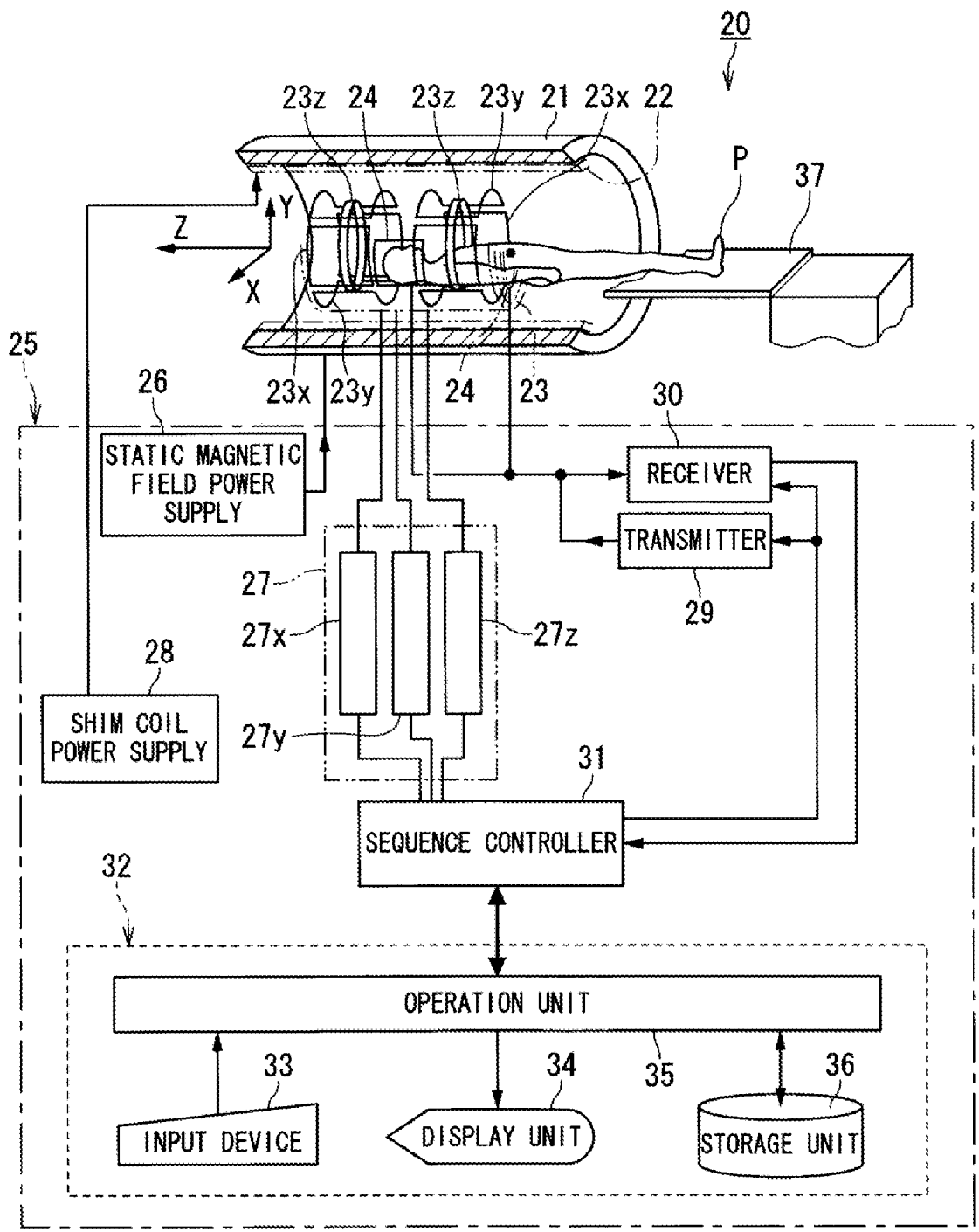
FIG. 1 is a block diagram showing a magnetic resonance imaging apparatus including a gradient coil unit according to an embodiment of the present invention.

FIG. 1 is a block diagram showing a magnetic resonance imaging apparatus including a gradient coil unit according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, a operation unit 35 and a storage unit 36.

The static field magnet 21 communicates with the static magnetic field power supply 26. The static magnetic field power supply 26 supplies electric current to the static field magnet 21 to get the function to generate a static magnetic field in a imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 has a function to transmit RF signals given from the transmitter 29 to the object P. The reception RF coil 24 has a function to receive MR signals generated due to nuclear spins inside the object P which are excited by the RF signals to give to the receiver 30.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a MR signal and A/D (analog to digital) conversion to the MR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Specifically, the computer 32 has a function to set imaging conditions including a pulse sequence and output the set imaging conditions to the sequence controller 31, and a function to generate MR image data by data processing including image reconstruction processing based on MR signals output from the sequence controller 31.

Thus, MR imaging of an object P can be performed by transmitting RF signals from the RF coils 24 in a state in which gradient magnetic fields and the static magnetic field are formed by the gradient coil unit 23 and the static field magnet 21, under the control by the control system 25. That is, an imaging system to perform MR imaging of an object P is formed with elements including the gradient coil unit 23, the static field magnet 21, the RF coils 24 and the control system 25.

Figure 2:
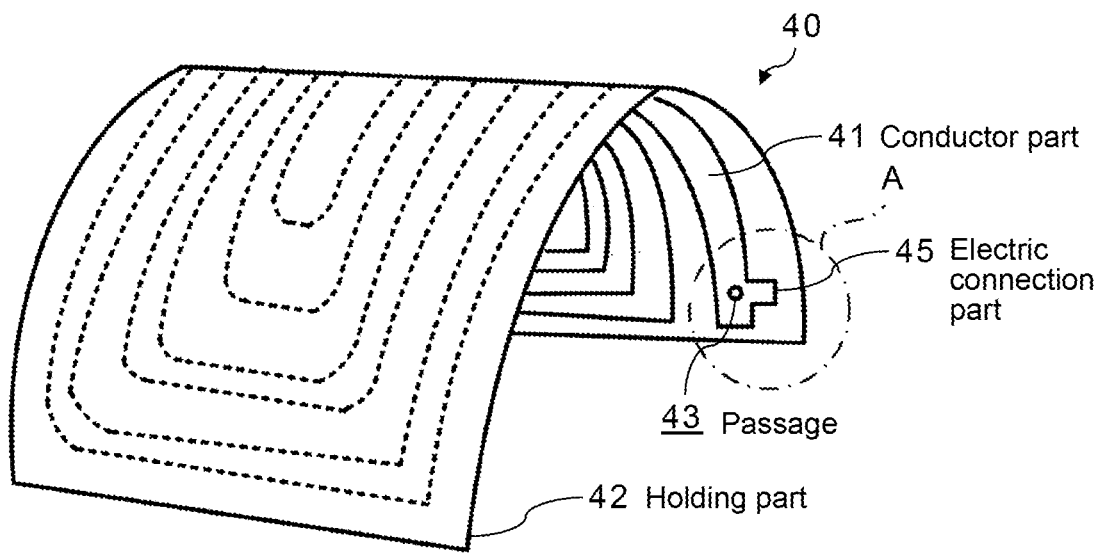
FIG. 2 is an oblique view showing a detailed structure of a saddle coil, for the magnetic resonance imaging apparatus, which composes the gradient coil unit shown in FIG. 1.
Figure 3:
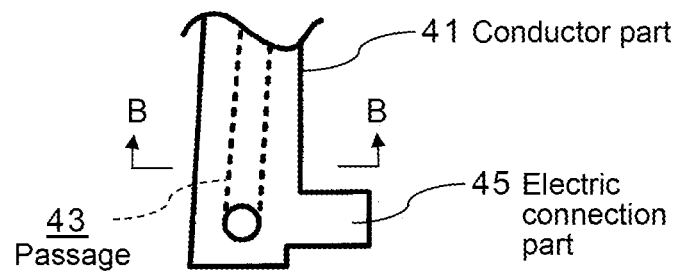
FIG. 3 is a partial enlarged view of a conductor part in the region A of the saddle coil shown in FIG. 2.
Figure 4:
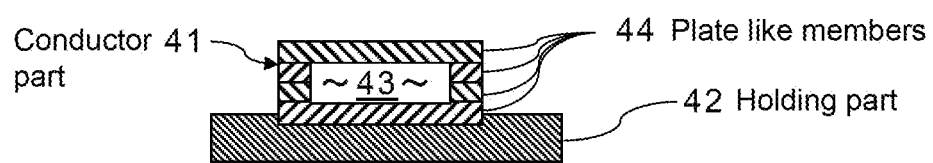
FIG. 4 is a transverse sectional view of the conductor part at the position B-B shown in FIG. 3.

FIG. 2 is an oblique view showing a detailed structure of a saddle coil 40, for the magnetic resonance imaging apparatus 20, which composes the gradient coil unit 23 shown in FIG. 1. FIG. 3 is a partial enlarged view of a conductor part 41 in the region A of the saddle coil 40 shown in FIG. 2. FIG. 4 is a transverse sectional view of the conductor part 41 at the position B-B shown in FIG. 3.

The saddle coil 40 has the conductor part 41 along a coil pattern and a holding part 42 holding the coil pattern. Specifically, the conductor part 41 is formed along the spiral coil pattern and the curved platy saddle coil 40 is formed by the holding part 42. Therefore, a magnetic flux for gradient magnetic field is formed in the direction passing through the center of the spiral conductor part 41.

The conductor part 41 can consist of an arbitrary coil material, such as copper, which has the conductive property. On the other hand, the holding part 42 can consist of an insulating material, for example, a compound material, having the insulation property, obtained by mixing a filler, such as silica, with an epoxy resin. Then, the conductor part 41 can be fixed to the holding part 42 by an arbitrary method. For example, the holding part 42 for fixing the platy conductor part 41 can be formed by hardening a compound material in a state where the conductor part 41 is soaked in the compound material. That is, the holding part 42 functions as a fixing part for fixing the conductor part 41 so as to be platy.

Note that, instead of the structure to fit a part of the conductor part 41 in the plate-like holding part 42 as illustrated in FIG. 4, the conductor part 41 may be completely buried in the holding part 42 so that a step does not arise between the conductor part 41 and the holding part 42. In this case, the holding part 42 may fill the interspace of the conductor part 41 to fix the conductor part 41 so as to be platy. On the contrary, one surface of the conductor part 41 of which cross sections are rectangular may be bonded to the surface of the plate-like holding part 42 with an adhesive agent or the like.

Furthermore, as another example, an insulating sheet which has flexibility may be provided between the holding part 42 and the conductor part 41. In that case, the holding part 42 can consist of an arbitrary material having a necessary stiffness.

Furthermore, a passage 43 of a coolant which uses at least a part of conductor part 41 as a wall surface is formed. As a coolant, an arbitrary cooling medium such as cooling water can be used. In the illustrated example, the passage 43 of the coolant whose wall surface is formed by the conductor part 41 has been formed inside the conductor part 41. For this reason, the coolant can be contacted directly with the conductor part 41 which composes the coil so that the conductor part 41 can be cooled.

Note that, when the passage 43 of the coolant is formed outside the conductor part 41, it is desired to make the passage 43 of the coolant adjacent to the conductor part 41 from a viewpoint of improving the cooling efficiency of the conductor part 41. That is, it is desired to form the passage 43 of the coolant so that at least a part of wall surfaces of the passage 43 is made by the conductor part 41. In that case, a passage of the coolant which uses the conductor part 41 and the holding part 42 as wall surfaces is formed. However, as illustrated, forming the passage 43 of the coolant inside the conductor part 41 is most effective.

The conductor part 41 can be made by laminating and bonding plate-like members 44 having spaces, such as grooves or notches, at positions corresponding to the passage 43 as shown in FIG. 4 and each consisting of a conducting material such as a metal plate. Then, the conductor part 41 along a saddle shape can be manufactured by bending and forming the plate-like members 44 before the lamination or after the bond.

Note that, the bonding method of the plate-like members 44 is arbitrary. When metal plates are bonded as the plate-like members 44, diffusion bonding of the metal plates leads to simplified manufacturing. The diffusion bonding is a method for bonding metals to be a bonding target by heating and pressurizing the metals to diffuse their atoms.

The diffusion bonding is classified into liquid phase diffusion bonding and solid phase diffusion bonding. The solid phase diffusion bonding is the diffusion bonding technique to bond solid metals with each other by heating and pressurizing them. On the other hand, the liquid phase diffusion bonding is the diffusion bonding technique to bond metals with each other by providing an insertion material between the metals to be the bonding target and melting the insertion material.

Each of the diffusion bonding techniques can be used to manufacture the conductor part 41. When the conductor part 41 is made by the diffusion bonding of multiple metal plates, it is practically difficult to specify the interfaces between the plate-like members 44 as shown in FIG. 4.

On the other hand, multiple plate-like members may be bonded by not only the diffusion bonding but another bonding method such as explosion bonding, insulation displacement contact, soldering, brazing, or bonding with an adhesive. Therefore, the interfaces and/or the bonding phases between multiple plate-like members may be specified according to the bonding method.

Both end parts of the conductor part 41 which forms the coil are used as electric connection parts. In the illustrated example, an electric connection part has been formed as a projection part 45 at the end part, of the conductor part 41, corresponding to the edge side of the saddle coil 40.

When the conductor part 41 is made by laminating the plate-like members 44 as mentioned above, the flexibility in the structure of the passage 43 of the coolant which is provided along the conductor part 41 can be increased. Therefore, the passage 43 of the coolant of which cross section area is not constant can be formed inside at least one of the holding part 42 and the conductor part 41. Accordingly, the passage 43 of the coolant of which cross section area is not constant can be formed so as to correspond to a density of the coil pattern.

For example, a thickness of the conductor part 41 at a position near the center of the saddle coil 40 is relatively thicker than a thickness of the conductor part 41 at a position near the edge of the saddle coil 40, as illustrated in FIG. 2. Accordingly, the cross section area of the passage 43 of the coolant can be also changed so as to match the sizes of the conductor part 41. That is, the sizes of the cross section areas of the passage 43 of the coolant can correspond to the density of the coil pattern.

Specifically, it is preferred that the cross section area of the passage 43 is relatively large at a position where the width of the conductor part 41 is relatively large while the cross section area of the passage 43 is relatively small at a position where the width of the conductor part 41 is relatively small. Thereby, the pressure loss of the coolant can be reduced.

Moreover, at least one of a passage 43 of the coolant which branches off and an interfluent passage 43 of the coolant may also be formed inside at least one of the holding part 42 and the conductor part 41. Thereby, the cooling effect can be improved by guiding the coolant locally to each position, where the density of the conductor is high and also a high heat generation is assumable, and the like.

Figure 5:
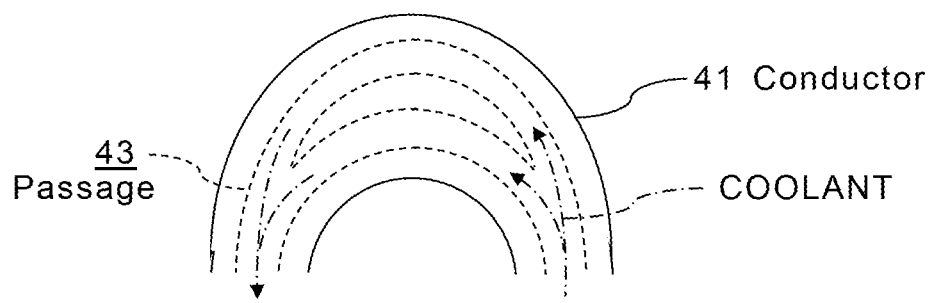
FIG. 5 shows the first example of forming a branching and confluent passage of the coolant in the saddle coil used as a component of the gradient coil unit shown in FIG. 1.

FIG. 5 shows the first example of forming a branching and confluent passage 43 of the coolant in the saddle coil 40 used as a component of the gradient coil unit 23 shown in FIG. 1.

As shown in FIG. 5, the passage 43 of the coolant which branches off once and then joins together again can be formed along the conductor part 41 according to the sizes of the conductor part 41. Forming such a branching and/or confluent passage 43 of the coolant allows local cooling of the conductor part 41 with securing the strength of the conductor part 41.

Figure 6:
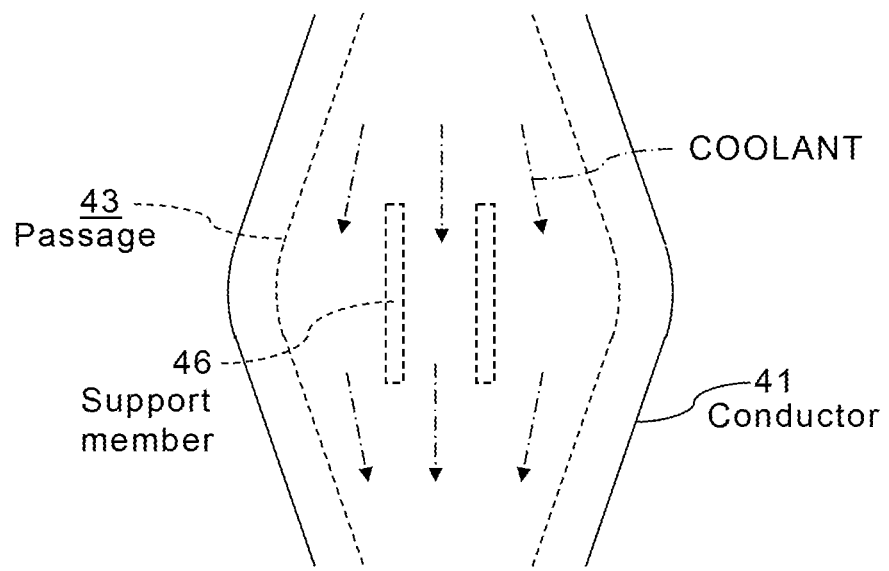
FIG. 6 shows the second example of forming a branching and confluent passage of the coolant in the saddle coil used as a component of the gradient coil unit shown in FIG. 1.

FIG. 6 shows the second example of forming a branching and confluent passage 43 of the coolant in the saddle coil 40 used as a component of the gradient coil unit 23 shown in FIG. 1.

When a width of the passage 43 of the coolant is enlarged in accordance with a width of the conductor part 41, the strength of the conductor part 41 may be decreased. Accordingly, plate-like support members 46 along the flow of the coolant can be provided inside the passage 43 as shown in FIG. 6. Thereby, the decrease in the strength of the conductor part 41 can be avoided. The case shown in FIG. 6 also involves a branching and confluence of the passage 43 of the coolant since the plate-like support members 46 function as partition plates.

Not only in the example shown in FIG. 6 but in a case where the passage 43 of the coolant is branched off or confluent and a case where the cross section area of the passage 43 of the coolant is changed, some reinforcement members each having an arbitrary shape, such as a plate-like shape, a tubular shape or a net-like shape, may be provided as necessary.

Moreover, a feed opening and a vent of the coolant having arbitrary structures are formed at the end parts of the passage 43 of the coolant.

Figure 7:
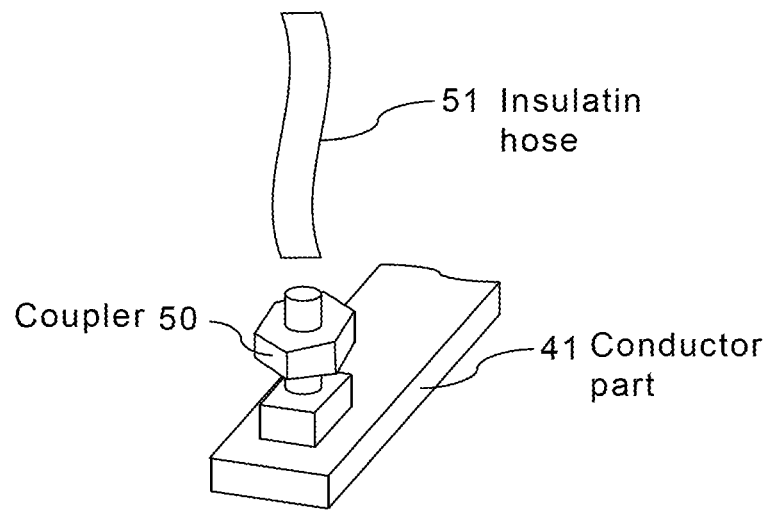
FIG. 7 is an oblique view showing the first example of structure at the end part of the passage of the coolant shown in FIG. 3 and FIG. 4.

FIG. 7 is an oblique view showing the first example of structure at the end part of the passage 43 of the coolant shown in FIG. 3 and FIG. 4.

A hole which connects the passage 43 of the coolant, formed inside the conductor part 41, with the outside of the conductor part 41 may be formed on the surface, facing the imaging area side, of the conductor part 41. Then, a coupler 50 can be attached to the hole as shown in FIG. 7. The hole on the conductor part 41 can be formed by an arbitrary method such as etching. Meanwhile, the coupler 50 can be attached to the conductor part 41 by an arbitrary method such as brazing. Thus, the passage 43 of the coolant can be connected with a circulating system of the coolant by attaching an insulating hose 51 to the coupler 50.

Figure 8:
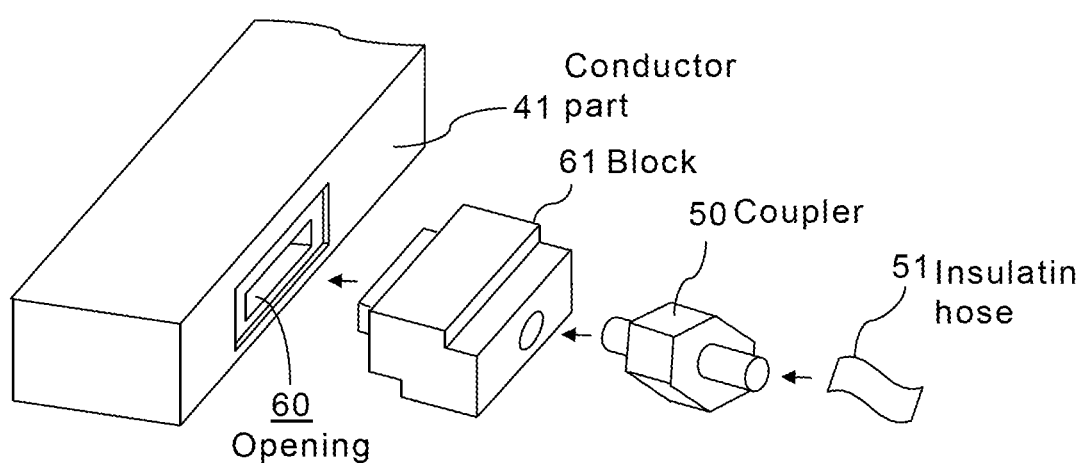
FIG. 8 is an oblique view showing the second example of structure at the end part of the passage of the coolant shown in FIG. 3 and FIG. 4.

FIG. 8 is an oblique view showing the second example of structure at the end part of the passage 43 of the coolant shown in FIG. 3 and FIG. 4.

As shown in FIG. 8, a hole to connect the passage 43 of the coolant with the outside of the conductor part 41 may also be formed on a lateral side of the conductor part 41. In this case, the passage 43 of the coolant can also be connected with a circulating system of the coolant using a coupler 50 and an insulating hose 51.

In addition, in the example shown in FIG. 8, a rectangular opening part 60 is formed on the lateral side of the conductor part 41 and the coupler 50 is attached to the conductor part 41 through a block 61 which can be fitted in the rectangular opening part 60. The block 61 for mounting the coupler 50 can be fixed to the conductor part 41 by an arbitrary bonding method such as brazing.

Then, a feed opening and an outlet of the coolant are provided, on both ends of the conductor part 41, with arbitrary structures as illustrated in FIG. 7 or FIG. 8. For example, the end part in the center side of the conductor part 41 may have a structure as illustrated in FIG. 7 while the other end part in an edge side of the saddle coil 40 may have a structure as illustrated in FIG. 8.

By the way, as mentioned above, the gradient coil unit 23 includes the multiple gradient coils for forming gradient magnetic fields in the three axis directions orthogonal to each other. Specifically, the gradient coil unit 23 has the X-axis gradient coil 23x, the Y-axis gradient coil 23y, and the Z-axis gradient coil 23z for respectively forming gradient magnetic fields in the X-axis direction, the Y-axis direction, and the Z-axis direction which are orthogonal to each other as the three axis directions.

The Z-axis gradient coil 23z is a gradient coil to form a gradient magnetic field in the Z-axis direction which is the axial direction of the cylindrical gradient coil unit 23. Therefore, the Z-axis gradient coil 23z is typically a cylindrical gradient coil.

On the other hand, the X-axis gradient coil 23x is a gradient coil to form a gradient magnetic field in the X-axis direction which is the horizontal direction perpendicular to the axial direction of the cylindrical gradient coil unit 23. Therefore, the X-axis gradient coil 23x has a spiral coil pattern to generate magnetic flux lines in the horizontal X-axis direction and is a saddle type gradient coil curved along the outline of the cylindrical gradient coil unit 23.

Moreover, the Y-axis gradient coil 23y is a gradient coil to form a gradient magnetic field in the Y-axis direction which is the vertical direction. Therefore, the Y-axis gradient coil 23y has a spiral coil pattern to generate magnetic flux lines in the vertical direction and is a saddle type gradient coil curved along the outline of the cylindrical gradient coil unit 23.

Therefore, the above mentioned saddle coil 40 composed by the spiral conductor part 41 having a curved plate-shape and fixed by the holding part 42 can be used as a gradient coil for at least one of the X-axis gradient coil 23x and the Y-axis gradient coil 23y. That is, the gradient coil unit 23 can be composed using the illustrated saddle coil 40 as at least one of the X-axis gradient coil 23x and the Y-axis gradient coil 23y.

In that case, at least one of the X-axis gradient coil 23x and the Y-axis gradient coil 23y has the conductor part 41 and the holding part 42, and the passage 43 of the coolant which uses at least a part of the conductor part 41 as a wall surface and whose cross section area is not constant is formed inside at least one of the holding part 42 and the conductor part 41.

When the saddle coil 40 is arranged in the illustrated direction so that the saddle coil 40 can form a gradient magnetic field in the vertical direction, the saddle coil 40 is used as the Y-axis gradient coil 23y. When the saddle coil 40 is used as the X-axis gradient coil 23x, the saddle coil 40 is arranged so that a gradient magnetic field can be formed in the horizontal direction, i.e., the center axis of the spiral coil pattern becomes the horizontal direction.

Therefore, the gradient coil unit 23 may be composed by a pair of the X-axis gradient coils 23x consisting of two saddle coils 40 arranged right and left along a cylinder and a pair of the Y-axis gradient coils 23y consisting of two saddle coils 40 arranged up and down along a cylinder.

Figure 9:
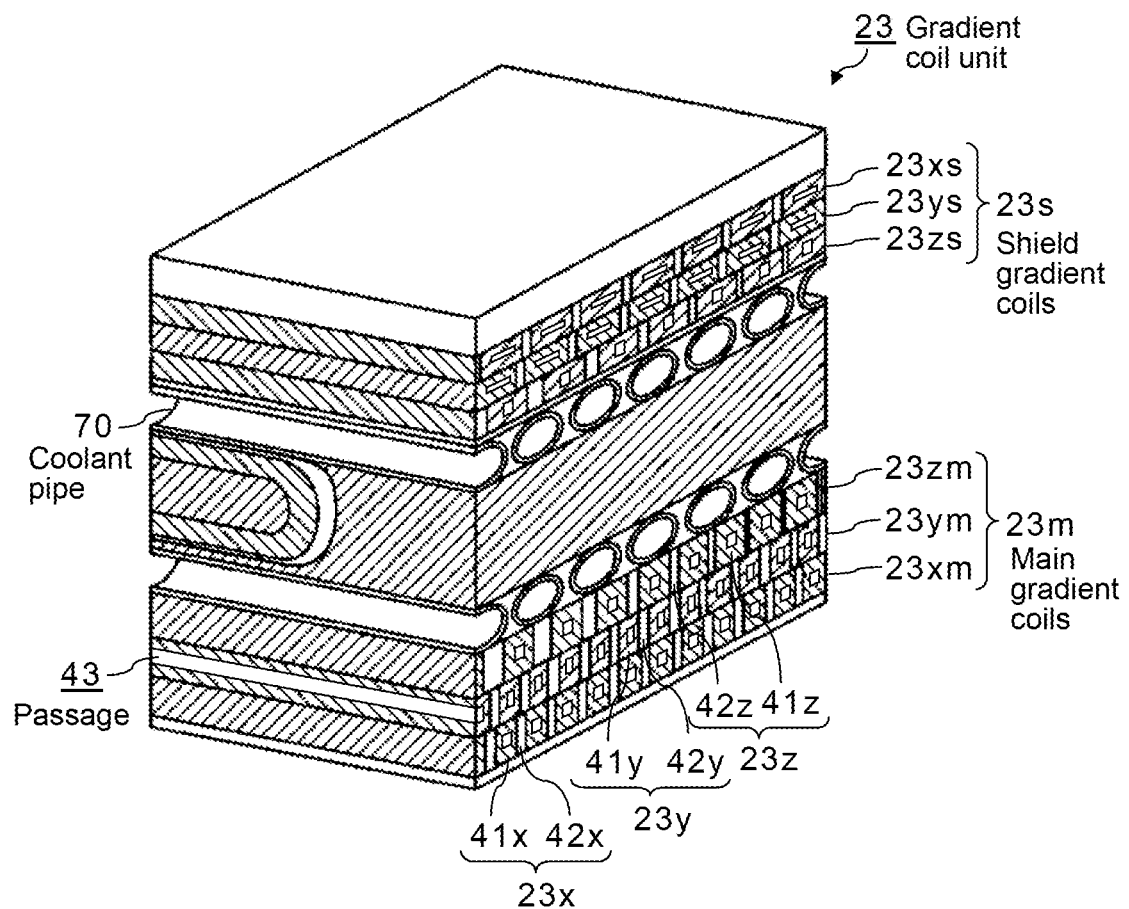
FIG. 9 shows an example of detailed structure of the X-axis gradient coil, the Y-axis gradient coil, and the Z-axis gradient coil shown in FIG. 1.

FIG. 9 shows an example of detailed structure of the X-axis gradient coil 23x, the Y-axis gradient coil 23y, and the Z-axis gradient coil 23z shown in FIG. 1.

As shown in FIG. 9, the gradient coil unit 23 has the X-axis gradient coil 23x, the Y-axis gradient coil 23y, and the Z-axis gradient coil 23z. The X-axis gradient coil 23x, the Y-axis gradient coil 23y, and the Z-axis gradient coil 23z are composed by an X-axis main coil 23xm and an X-axis shield coil 23xs arranged outside the X-axis main coil 23xm, a Y-axis main coil 23ym and a Y-axis shield coil 23ys arranged outside the Y-axis main coil 23ym, and a Z-axis main coil 23zm and a Z-axis shield coil 23zs arranged outside the Z-axis main coil 23zm respectively.

The X-axis main coil 23xm is composed by the first conductor part 41x along a coil pattern of the X-axis gradient coil 23x and the first holding part 42x holding the coil pattern of the X-axis gradient coil 23x. The Y-axis main coil 23ym is composed by the second conductor part 41y along a coil pattern of the Y-axis gradient coil 23y and the second holding part 42y holding the coil pattern of the Y-axis gradient coil 23y. The Z-axis main coil 23zm is composed by the third conductor part 41z along a coil pattern of the Z-axis gradient coil 23z and the third holding part 42z holding the coil pattern of the Z-axis gradient coil 23z.

At least one cooling pipe 70 for flowing the coolant can be provided between the shield coil 23s and the main coil 23m. In the illustrated example, the cooling pipe 70 is provided in each of the shield coil 23s side and the main coil 23m side. Thus, the Z-axis main coil 23zm, the Y-axis main coil 23ym and the X-axis main coil 23zm can be arranged in this order from the side close to the cooling pipe 70. On the other hand, the Z-axis shield coil 23zs, the Y-axis shield coil 23ys, and the X-axis shield coil 23xs can be arranged in this order from the side close to the cooling pipe 70.

Furthermore, as mentioned above, at least one of the X-axis gradient coil 23x and the Y-axis gradient coil 23y can consist of the saddle coil 40 as shown in FIG. 2. That is, the passage 43 of the coolant which uses at least a part of the conductor part 41x, 41y as a wall surface can be formed in at least one of the X-axis gradient coil 23x and the Y-axis gradient coil 23y. Moreover, the passage 43 of the coolant of which cross section area is not constant can be formed inside at least one of the holding part 42x, 42y and the conductor part 41x, 41y which compose at least one of the X-axis gradient coil 23x and the Y-axis gradient coil 23y.

In the example shown in FIG. 9, each of the X-axis gradient coil 23x and the Y-axis gradient coil 23y has consisted of the saddle coil 40. Furthermore, the passage 43 of the coolant of which cross section area is not constant can be formed also in the Z-axis gradient coil 23z which has the third conductor part 41z along a spiral coil pattern and the third holding part 42z to fix the third conductor part 41z into a cylindrical and platy form. Further, the passage 43 of the coolant which uses at least a part of the third conductor part 41z as a wall surface can be formed.

That is, at least one of the passage 43 of the coolant of which cross section area is not constant and the passage 43 of the coolant which uses at least a part of the conductor 41x, 41y and 41z as a surface of wall can be formed in all the X-axis gradient coil 23x, the Y-axis gradient coil 23y and the Z-axis gradient coil 23z.

In the illustrated example, the passage 43 of the coolant of which cross section area is not constant has been formed in each of the inside of at least one of the first conductor part 41x and the first holding part 42x, the inside of at least one of the second conductor part 41y and the second holding part 42y, and the inside of at least one of the third conductor part 41z and the third holding part 42z. Further, the passage 43 of the coolant whose wall surfaces are formed by the first conductor part 41x, the passage 43 of the coolant whose wall surfaces are formed by the second conductor part 41y, and the passage 43 of the coolant whose wall surfaces are formed by the third conductor part 41z have been formed in the X-axis gradient coil 23x, the Y-axis gradient coil 23y, and the Z-axis gradient coil 23z respectively.

Note that, the X-axis shield coil 23xs, the Y-axis shield coil 23ys and the Z-axis shield coil 23zs may also have structures similar to those of the X-axis main coil 23xm, the Y-axis main coil 23ym and the Z-axis main coil 23zm, as shown in FIG. 9. That is, the passage 43 of the coolant of which cross section area is not constant can also be formed in each of the X-axis shield coil 23xs, the Y-axis shield coil 23ys and the Z-axis shield coil 23zs.

For this reason, the X-axis gradient coil 23x, the Y-axis gradient coil 23y and the Z-axis gradient coil 23z can be cooled effectively. Therefore, the cooling pipes 70 provided between the shield coil 23s and the main coil 23m may be omitted.

Note that, each of the X-axis gradient coil 23x and the Y-axis gradient coil 23y may be a gradient coil which has a shape other than the saddle coil 40.

Therefore, at least one of multiple gradient coils to form gradient magnetic fields in the three axis directions orthogonal to each other can be composed by the conductor part 41 along a coil pattern and the holding part 42 which holds the coil pattern, and then the passage 43 of the coolant of which cross section area is not constant can be formed inside at least one of the holding part 42 and the conductor part 41. Further, the passage 43 of the coolant which uses at least a part of conductor part 41 as a wall can be formed.

As described above, the gradient coil unit 23 of the magnetic resonance imaging apparatus 20 has a passage 43 of a coolant, such as cooling water, inside or adjacent to a conductor composing a coil. In addition, the gradient coil unit 23 has a passage 43 of a coolant of which cross section area is not constant.

In the case of the conventional cooling method using pipes for cooling water, coils are indirectly cooled through walls of the pipes. For this reason, the cooling efficiency of the coils is limited. Moreover, gradient coils for the X-axis and the Y-axis are spiral. For this reason, the work to twist a hollow copper pipe around each gradient coil has been needed. Specifically, the work to form the copper pipe by inserting and bending the copper pipe along grooves of a winding mold has been needed. Such work increases labors and manufacturing costs.

On the contrary, the conductors of the gradient coil unit 23 can be cooled directly by a coolant since at least a part of the walls which forms the passage 43 of the coolant is the conductor itself composing the coil. Moreover, when the conductor part 41 is made by laminating metal plates by a bonding method such as the diffusion bonding technique, the width and the pathway of the passage 43 can be determined arbitrarily. For this reason, even in case of a spiral coil, the passage 43 can be formed easily inside the conductor part 41 or close to the conductor part 41. In addition, the passage 43 of the coolant can be optimized according to a temperature distribution of the coil.

As a result, the cooling efficiency of the gradient coil unit 23 can be improved. Thereby, the waiting time required to cool the coil between imaging can be shortened. Therefore, a time spared for imaging can be increased.

Moreover, the temperature of the gradient coil unit 23 can be maintained constant. For this reason, temperature changes in iron shims for magnetic field adjustment placed in the gradient coil unit 23 can also be prevented. Therefore, in addition to a power loss due to an increase in a resistance of each coil which composes the gradient coil unit 23 and degradation in an image quality due to abnormality in a gradient magnetic field waveform, degradation in an image quality due to the non-uniformity of the static magnetic field and a defect in fat suppression due to a center frequency shift can also be decreased. Besides, burdens of patients can be reduced and the throughput can be improved since the time required for correcting the static magnetic field and the gradient magnetic fields can be shortened.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A gradient coil unit configured for a magnetic resonance imaging apparatus comprising:
    gradient coils configured for forming gradient fields in mutually orthogonal three axis directions,
    wherein at least one of said gradient coils includes:
        a gradient current conductor part extending along a coil pattern; and
        a holding part holding the gradient current conductor part that extends along the coil pattern, securely in place along said coil pattern, wherein at least a portion of an outer surface of said gradient current conductor part, along said coil pattern is not in contact with said holding part, and wherein a coolant passage for transmission of a coolant is formed at least partially inside of or within the at least one gradient coil conductor part, the formed coolant passage having a non-constant cross-sectional area extending along said coil pattern.

2. A gradient coil unit for a magnetic resonance imaging apparatus of claim 1 comprising:

an X-axis gradient coil, a Y-axis gradient coil, and a Z-axis gradient coil for forming gradient magnetic fields respectively in mutually orthogonal an X-axis direction, a Y-axis direction, and a Z-axis direction as the three axis directions, said X-axis gradient coil, said Y-axis gradient coil, and said Z-axis gradient coil having:

a first gradient current conductor part along a coil pattern of said X-axis gradient coil;

a first holding part holding the coil pattern of said X-axis gradient coil;

a second gradient current conductor part along a coil pattern of said Y-axis gradient coil;

a second holding part holding the coil pattern of said Y-axis gradient coil;

a third gradient current conductor part along a coil pattern of said Z-axis gradient coil; and a third holding part holding the coil pattern of said Z-axis gradient coil, wherein at least a portion of an outer surface of at least one of said first, second or third gradient current conductor part is not in contact with corresponding said first, second or third holding part, and wherein the coolant passage for transmission of the coolant is formed inside at least one of said X-axis gradient coil, Y-axis gradient coil and Z-axis gradient coil and is surrounded by at least one of said first gradient current conductor part, said first holding part, said second gradient current conductor part, said second holding part, said third gradient current conductor part and said third holding part, the passage having a non-constant cross section area along a coil pattern.

3. A magnetic resonance imaging apparatus comprising:
said gradient coil unit of claim 1; and
an imaging system configured to perform magnetic resonance imaging of an object using said gradient coil unit.

4. A gradient coil unit for a magnetic resonance imaging apparatus of claim 1, wherein the coolant passage is formed inside said gradient current conductor part, said gradient current conductor part forming a wall surface of the coolant passage.

5. A gradient coil unit for a magnetic resonance imaging apparatus of claim 1, wherein said gradient current conductor part and said holding part jointly form a wall surface of the passage for coolant to flow along while simultaneously in contact with both said gradient current conductor part and said holding part along the coil pattern.

6. A gradient coil unit for a magnetic resonance imaging apparatus of claim 1, wherein said gradient current conductor part consists of laminated and bonded platy members forming a void corresponding to the coolant passage, each of the platy members consisting of a conductive material.

7. A gradient coil unit for a magnetic resonance imaging apparatus of claim 6, wherein said gradient current conductor part consists of the platy members bonded by diffusion bonding.

8. A gradient coil unit for a magnetic resonance imaging apparatus of claim 1, wherein at least one of a branching passage of the coolant passage and a confluent passage of the coolant passage is formed inside said gradient current conductor part.

9. A gradient coil unit for a magnetic resonance imaging apparatus of claim 1, wherein the non-constant cross section area of the coolant passage increases in correspondence with increases in density of the coil pattern.

10. A gradient coil unit for a magnetic resonance imaging apparatus of claim 1, wherein said holding part consists of an insulating material.

11. A gradient coil unit for a magnetic resonance imaging apparatus of claim 1, wherein an insulating sheet is arranged between said holding part and said gradient current conductor part.

12. A gradient coil unit for a magnetic resonance imaging apparatus of claim 1 comprising:

an X-axis gradient coil, a Y-axis gradient coil, and a Z-axis gradient coil for forming gradient magnetic fields respectively in mutually orthogonal an X-axis direction, a Y-axis direction, and a Z-axis direction as the three axis directions, wherein at least one of said X-axis gradient coil and said Y-axis gradient coil includes:

said gradient current conductor part; and
said holding part, and wherein the coolant passage is formed inside at least one of said gradient current conductor part and said holding part.

13. A method for manufacturing a gradient coil unit for a magnetic resonance imaging apparatus comprising:

positioning and laminating plural platy members together along a coil pattern of the gradient coil unit so as to form a void corresponding to a coolant passage located inside the laminated platy members, each of the platy members consisting of a conductive material that together form a gradient current conductor part; and bonding said gradient current conductor part made of laminated platy members to an electrical insulating holding part which holds the gradient current conductor part of laminated platy members securely in place along said coil pattern, wherein at least a portion of an outer surface of said laminated platy members along the coil pattern is not in contact with said bonded electrical insulating holding part, and wherein the platy members are formed so as to create said coolant passage having a non-constant cross-sectional area extending along the coil pattern.

* * * * *